US009708634B2

(12) United States Patent
López-Cervantes

(10) Patent No.: US 9,708,634 B2
(45) Date of Patent: *Jul. 18, 2017

(54) PROCESS FOR MAKING CHITIN DERIVATIVES

(71) Applicant: Agrinos AS, Lysaker (NO)

(72) Inventor: Jaime López-Cervantes, Sonora (MX)

(73) Assignee: Agrinos AS, Lysaker (NO)

( * ) Notice: Subject to any disclaimer, the term of this patent is extended or adjusted under 35 U.S.C. 154(b) by 0 days.

This patent is subject to a terminal disclaimer.

(21) Appl. No.: 14/577,999

(22) Filed: Dec. 19, 2014

(65) Prior Publication Data

US 2015/0111255 A1   Apr. 23, 2015

Related U.S. Application Data

(63) Continuation of application No. 13/530,552, filed on Jun. 22, 2012, now abandoned.

(60) Provisional application No. 61/500,527, filed on Jun. 23, 2011.

(51) Int. Cl.
    *C12P 19/26* (2006.01)
    *C12P 19/04* (2006.01)
    *C12N 9/20* (2006.01)

(52) U.S. Cl.
    CPC ............... *C12P 19/26* (2013.01); *C12N 9/20* (2013.01); *C12P 19/04* (2013.01)

(58) Field of Classification Search
    CPC ............ C12P 19/26; C12P 19/04; C12N 9/20
    USPC ...................................................... 435/252.4
    See application file for complete search history.

(56) References Cited

U.S. PATENT DOCUMENTS

| 4,536,207 A | 8/1985 | McCandliss |
| 4,812,159 A | 3/1989 | Freepons |
| 4,952,229 A | 8/1990 | Muir |
| 4,964,894 A | 10/1990 | Freepons |
| 4,978,381 A | 12/1990 | Hadwiger |
| 5,266,096 A | 11/1993 | Slavensky |
| 5,374,627 A | 12/1994 | Ito et al. |
| 5,733,851 A | 3/1998 | Villanueva |
| 5,998,173 A | 12/1999 | Haynes et al. |
| 6,060,429 A | 5/2000 | Ben-Shalom |
| 6,232,270 B1 | 5/2001 | Branly |
| 6,407,040 B1 | 6/2002 | Nichols |
| 6,524,998 B1 | 2/2003 | Kloepper et al. |
| 6,649,566 B2 | 11/2003 | Doostar |
| 6,979,664 B1 | 12/2005 | Smith et al. |
| 7,241,463 B2 | 7/2007 | Nielsen |
| 7,250,068 B1 | 7/2007 | Smith et al. |
| 8,748,124 B2 | 6/2014 | Lopez-Cervantes et al. |
| 9,253,989 B2 | 2/2016 | Smith et al. |
| 2010/0267999 A1 | 10/2010 | Lau et al. |
| 2012/0084886 A1 | 4/2012 | López-Cervantes |
| 2015/0257393 A1 | 9/2015 | Nijak et al. |

FOREIGN PATENT DOCUMENTS

| CN | 1269405 | 4/1999 |
| CN | 1314951 | 9/2001 |
| CN | 101130799 | 2/2008 |
| CN | 101223282 | 7/2008 |
| JP | 2003160420 | 6/2003 |
| KR | 20050117990 | 12/2005 |
| WO | WO 89/01288 | 2/1989 |
| WO | WO 97/031121 | 8/1997 |
| WO | WO 03/068824 | 8/2003 |
| WO | WO 2011/076759 | 6/2011 |
| WO | WO 2011/157747 | 12/2011 |
| WO | WO 2012/175739 | 12/2012 |

OTHER PUBLICATIONS

Aye and Stevens, "Technical Note: Improved chitin production by pretreatment of shrimp shell," *Journal of Chemical Technology and Biotechnology*, vol. 79, pp. 421-425, 2004.

Bhaskar et al., "Shrimp biowaste fermentation with *Pediococcus acidolactici* CFR2182: Optimization of fermentation conditions by response surface methodology and effect of optimized conditions on deproteination/demineralization and carotenoid recovery," *Enzyme and Microbial Technology*, vol. 40, pp. 1427-1434, 2007.

Bhattacharya et al., "Bacterial Chitinases: Properties and Potential," *Critical Reviews in Biotechnology*, vol. 27, pp. 21-28, 2007.

Binod et al., "Fungal biosynthesis of endochitinase and chitobiase in solid state fermentation and their application for the production of N-acetyl-D-glucosamine from colloidal chitin," *Bioresource Technol.*, vol. 98, pp. 2742-2748, 2007.

Bueno-Solano et al., "Chemical and biological characteristics of protein hydrolysates from fermented shrimp by-products," *Food Chemistry*, vol. 112, pp. 671-675, 2009.

Campbell et al., "A study of Chitin-decomposing Micro-organisms of Marine Origin," *Journal of General Microbiology*, vol. 5, pp. 894-905, 1951.

Cira et al., "Pilot scale lactic acid fermentation of shrimp wastes for chitin recovery," Process Biochemistry, vol. 37, pp. 1359-1366, 2002.

(Continued)

*Primary Examiner* — Teresa E Knight
(74) *Attorney, Agent, or Firm* — Klarquist Sparkman, LLP

(57) ABSTRACT

Disclosed is a process comprising (1) forming an aqueous mixture comprising a microbial composition and solid chitin, wherein said microbial composition comprises one or more microbes that produce chitin digesting enzymes; and (2) fermenting the mixture for a time sufficient to enzymatically digest all or part of the chitin to form a fermented mixture comprising chitosan and glucosamine. In some embodiments, the chitin is derived from the biodegradation of chitin containing marine Arthropods. In other embodiments, the chitin is obtained from chitin containing fungi, filamentous fungi and yeast which is extracted via a chemical process. In yet another embodiment, the chitin is obtained by the biodegradation of chitin containing fungi, filamentous fungi, yeast and/or insects, preferably using HQE for the digestion. In some embodiments, the process is carried out with a solution that already contains chitosan and/or glucosamine such as HYTb, the aqueous fraction obtained from the biodegradation of chitin containing organisms.

11 Claims, 4 Drawing Sheets

(56) References Cited

OTHER PUBLICATIONS

Cody, "Distribution of Chitinase and Chitobiase in Bacillus," *Current Microbiology*, vol. 19, pp. 201-205, 1989.
Kandra et al., "Efficient use of shrimp waste: present and future trends," *Appl. Microbiol. Biotechnol.*, vol. 93, pp. 17-29, 2012.
López-Cervantes et al., "Analysis of free amino acids in fermented shrimp C1 waste by high-performance liquid chromatography," *Journal of Chromatography*, vol. 1105, Nos. 1-2, pp. 106-110, 2006.
Nandakumar et al., "Chitinolytic Activity of Native *Pseudomonas fluorescens* Strains," *Journal of Agriculture Science Technology*, vol. 9, pp. 61-68, 2007.
Sini et al., "Study on the production of chitin and chitosan from shrimp shell by using *Bacillus subtilis* fermentation," *Carbohydrate Research*, vol. 342, pp. 2423-2429, 2007.
Win et al., "Shrimp chitin as substrate for fungal chitin deacetylase," *Applied Microbiology & Biotechnology*, vol. 57, pp. 334-341, 2001.
Decision of Final Rejection issued by the Patent Office of the People's Republic of China on Apr. 7, 2016, for CN 201280030890. X, 8 pages (English translation).

PROCESS FOR MAKING CHITIN DERIVATIVES

CROSS-REFERENCE TO RELATED APPLICATIONS

This application is a continuation of co-pending U.S. patent application Ser. No. 13/530,552, filed Jun. 22, 2012, which claims the benefit of U.S. Provisional Patent Application Ser. No. 61/500,527, filed Jun. 23, 2011, pursuant to 35 C.F.R. 119(e) and is incorporated herein in its entirety.

BACKGROUND OF THE INVENTION

Chitin, poly ($\beta$(1-4)-N-acetyl-D-glucosamine) is a natural polysaccharide of mayor importance. This biopolymer is synthesized by an enormous number of living organisms including crustaceans, insects, fungi, filamentous fungi and yeasts. Considering the amount of chitin produced annually in the word, it is the most abundant polymer after cellulose.

The main commercial sources of chitin have been crab and shrimp shell. In industrial processing, chitin is extracted from crustaceans by acid treatment to dissolve calcium carbonate followed by alkaline extraction to solubilize proteins. The most important derivate of chitin is chitosan, obtained by (partial) deacetylation of chitin in the solid state under alkaline conditions (concentrate NaOH) or by enzymatic hydrolysis in the presence of chitin deacetylase. Under controlled conditions, chitin and chitosan can be polymerized to yield water soluble derivatives such as chitin-oligosaccharides (ChOS) and chitosan-oligosaccharides (COS), respectively.

These oligomers are recognized for their bioactivity; including anti-tumor, bactericidal and fungicidal activity, eliciting chitinase and regulating plant growth. Chitin is involved in host defense against bacterial invasion, has been used to prepare affinity chromatography column and is widely used to immobilize enzymes and whole cells.

On account of its biodegradability, non-toxicity, physiological inertness, antibacterial properties, hydrophilicity, gel-forming properties and affinity for proteins, chitin has found applications in many areas other than food such as in biosensors. Chitin—based materials are also used for the treatment of industrial pollutants. Chitin can be processed in form of film and fiber. Regenerated chitin derivative fibers are used as binders in the paper making process, fiber improves the breaking strength of paper. However, the main development of chitin film and fiber is in medical and pharmaceutical applications as wound-dressing material.

When the degree of deacetylation of chitin reaches about 50% it become soluble in aqueous acidic media and is called chitosan. Chitosan is the only pseudo-natural cationic polymer and thus, it is used many applications. Being soluble in aqueous solution, it is largely used in different applications as solutions, gels, or films and fibers. The main investigations of chitosan concern its preparation with varied molecular weights and deacetylation, the dependence of its solution properties on the deacetylation, the preparation of derivatives and applications.

Chitosan is much easy to process than chitin, but the stability of chitosan materials is generally lower, owing to their more hydrophilic character and, especially, pH sensitivity. Chitosan and its derivatives have various functional properties that have made it possible for them to be used in many fields including, food, cosmetic, biomedicine, agriculture, environment protection and wastewater management. The most important fields where the specificity of chitosan must be recognized are cosmetic, pharmaceutical and biomedical applications. Drug delivery applications include oral, nasal, parenteral and transdermal administration, implants and gene delivery.

Another point to note is biological activity in regard to agriculture since chitosan exhibits antivirus and antiphage activities. It inhibits the growth of bacterial and bacterial infection, and stimuli the natural defenses in plant. Also is used for the seed coating, frost protection, time releases of fertilizers and nutrients into the soil.

Even though the chitosan is known to have important functional activities, the high molecular weight and high viscosity may restrict the uses in some special fields, particularly in medicine and the food industry, because most animal intestines, especially human gastrointestinal tract, do not possess enzymes such as chitinase and chitosanase, which directly degrade the $\beta$-glucosidic linkage in chitin and chitosan. Unlike chitosan, its hydrolyzed products and chitosan oligosaccharides (COS) are readily soluble in water duo their shorter chain length and free amino group in D-glucosamine units. The low viscosity and great solubility of COS at neutral pH have attracted the interest of many researchers to utilize chitosan in its oligosaccharide form. Especially, in food and nutrition areas have emphasized their ability to improve food and quality and human health progression.

Chemical and enzymatic methods are widely used for COS production and among them chemical hydrolysis is used more commonly in the industrial-scale production. However, chemical hydrolysis has some drawbacks to be commercialized, due to development of toxic compounds, higher risk associated with the environment pollution, and lower production yield. The enzymatic processes are generally carried out in bath and are preferable over chemical methods. This is due to minimized adverse chemical modifications of product during enzymatic hydrolysis.

Other product generated from chitin is glucosamine, IT can be used in agriculture, has shown that the presence of glucosamine in the composition of the soil cause an increment of trichomes absorbent, which is manifested in increased the vigor of the plant. The first reaction can be observed is a strengthening of the tips that take a deep green color, with the border of slightly curly leaves. This is because, when applying glucosamine in the soil, the plant induce a response similar to that which would result when la plant try to defender itself of the attack from fungus, nematodes or insect without these really exist.

In the area of medicine, glucosamine has been used for the treatment for arthritis, promotes the development of the cartilaginous tissue, is used in the reconstruction of cartilage. Glucosamine is involved in the formation of nails, tendons, skin, eyes, bones, ligaments and heart valves, is also implicated in the production of collagen and proteoglycans.

SUMMARY OF THE INVENTION

Disclosed are processes for increasing the chitosan and/or glucosamine in HYTb. The process comprises (1) forming a mixture comprising HYTb, a microbial composition and solid chitin, wherein said microbial composition comprises one or more microbes that produce chitin digesting enzymes; and (2) fermenting the mixture for a time sufficient to enzymatically digest all or part of said chitin to form a fermented mixture. The amount of at least one of chitosan and glucosamine in the fermented mixture is greater than in said HYTb.

In an alternative embodiment, the mixture is diluted to form a diluted mixture which is fermented to digest all or part of said chitin to form a fermented mixture. The absolute amount of at least one of chitin and glucosamine (taking into account the dilution step) in the fermented mixture is greater than that in HYTb.

In some embodiments HYTc is the source of said chitin. Generally, HYTc is micronized to form micronized chitin and residual chitin. The chitin used in the process can be the micronized chitin. However, since this form of chitin has other commercial uses, it is preferred that residual chitin be used in the process.

Depending on the extent of the chitin digestion and the ultimate use of the product of the process solids can be separated from the fermented mixture conveniently by centrifugation or filtering. If it is desired that the microbes in the microbial composition be retained, filtration is preferred although low g centrifugation can be used.

The source of chitin need not be from HYTc. For example, chitin derived from filamentous fungi and/or yeasts can be used. See, for example, U.S. Pat. No. 7,556,946 which discloses a chemical process to extract chitin from fungi, including filamentous fungi, and yeasts from groups including Zygomycetes, Basiomycetes, Ascomycetes and Deuteromycetes. Examples include *Aspergillum, Penicillium, Trichoderma, Saccaromyces* and *Schizosacaromyces* species and edible mushrooms such as *Agaricus, Pleurotus, Boletus* and *Lentinula* species.

In the preferred embodiments the microbial composition comprises HQE.

In another embodiment, the process comprises (1) mixing a marine animal or marine animal by-product with a first microbial composition to form a first mixture, where the first microbial composition contains one or more microbes that produce enzymes that digest the marine animal or by-product into solid, aqueous and lipid fractions, wherein the solid fraction comprises chitin and the aqueous phase comprises amino acids, chitosan and glucosamine; (2) fermenting the first mixture; (3) separating the first mixture into solid, aqueous and lipid fractions, where the solid fraction comprises chitin and the aqueous phase comprises chitosan and glucosamine; (4) forming a second mixture comprising the aqueous fraction, chitin and a second microbial composition, where the second microbial composition comprises one or more microbes that produce chitin digesting enzymes; (5) fermenting the second mixture to form a fermented second mixture; and (6) optionally, separating the fermented second mixture into a second aqueous fraction and second solid fraction, where the second aqueous fraction has a higher content of at least one of chitosan and glucosamine as compared to the first aqueous fraction.

As with the earlier described embodiments, the second mixture can be diluted to form a diluted second mixture which is then fermented to digest all or part of the chitin to form a second fermented mixture. The absolute amount of at least one of chitin and glucosamine in the second fermented mixture is greater than that in said first aqueous fraction.

HYTc is the preferred source of chitin. It can be micronized chitin or residual chitin.

In this multiphase fermentation process the first and second microbial compositions preferably comprises HQE.

In yet another embodiment, the process comprises (1) forming a mixture comprising a microbial composition and solid chitin, wherein said microbial composition comprises one or more microbes that produce chitin digesting enzymes; and (2) fermenting the mixture for a time sufficient to enzymatically digest all or part of the chitin to form a fermented mixture. The source of the chitin can be HYTc. Alternatively, the chitin can be derived from fungi, including filamentous fungi, and/or yeasts by a non enzymatic process. See e.g. U.S. Pat. No. 7,556,946.

Still further, the chitin and other useful products can be obtained from the biodegradation of chitin containing biological sources such as the fungi, including filamentous fungi, yeast and insects identified above. The process comprises: (1) mixing a chitin containing biological source, such as fungi, including filamentous fungi, yeast and/or insects, with a first microbial composition to form a first mixture, where the first microbial composition contains one or more microbes that produce enzymes that digest the chitin containing biological source into solid, aqueous and optionally lipid fractions, wherein the solid fraction comprises chitin and the aqueous phase comprises amino acids, chitosan and glucosamine; (2) fermenting the first mixture; (3) separating the first mixture into solid, aqueous and optionally lipid fractions, where the solid fraction comprises chitin and the aqueous phase comprises chitosan and glucosamine.

DETAILED DESCRIPTION OF PREFERRED EMBODIMENTS

Disclosed is a process comprising (1) forming an aqueous mixture comprising a microbial composition and solid chitin, wherein said microbial composition comprises one or more microbes that produce chitin digesting enzymes; and (2) fermenting the mixture for a time sufficient to enzymatically digest all or part of the chitin to form a fermented mixture comprising chitosan and glucosamine.

In some embodiments, the chitin is derived from the biodegradation of chitin containing marine Arthropods. In other embodiments, the chitin is obtained from chitin containing fungi, filamentous fungi and yeast which is extracted via a chemical process. See e.g. U.S. Pat. No. 7,556,946. In yet another embodiment, the chitin is obtained by the biodegradation of chitin containing fungi, including filamentous fungi, yeast and/or insects as disclosed herein.

In some embodiments, the process is carried out with a solution that already contains chitosan and/or glucosamine. The degradation of the solid chitin in the process produces more chitosan and/or glucosamine so that the final solution contains higher amounts of these components. In a preferred embodiment, the chitosan and/or glucosamine containing starting solution is HYTb. The solution obtained after fermentation is referred to as HYTd. HYTd, in some embodiments, is essentially HYTb with a higher concentration of chitosan and/or glucosamine. If, for example, HYTb contains 1.2 wt % chitosan and 1 wt % glucosamine, the resulting HYTd will contain higher concentrations of one or both of these components, preferably both of the components.

Sources of Chitin

1. Biodegradation of Chitin Containing Arthropods

Figure 1:
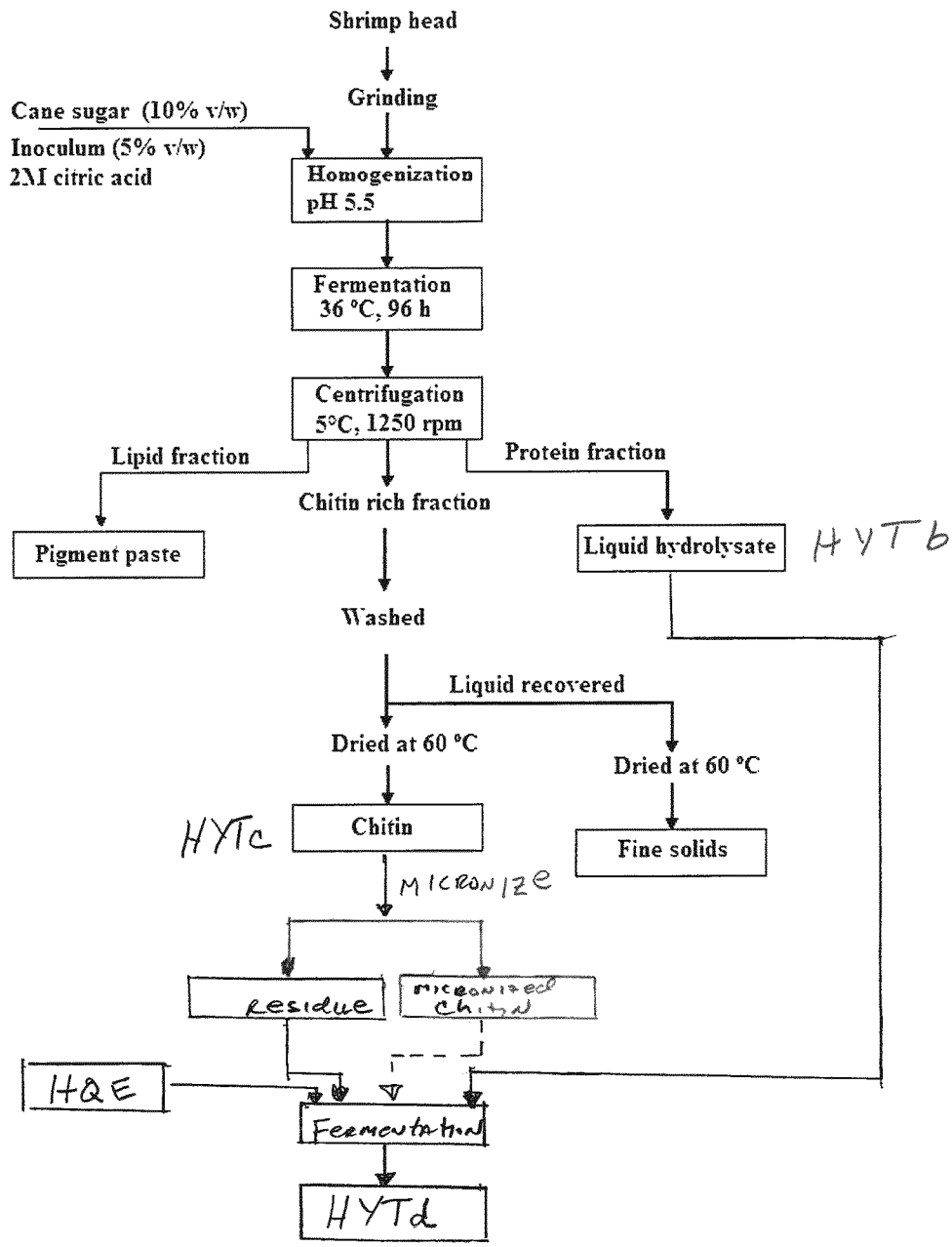
FIG. 1 is a flow diagram showing the digestion of crustacean to form HYTb and HYTc. The HYTc and HYTb are subsequently processed with HQE to form HYTd, a solution with relatively high amounts of chitosan and glucosamine as compared to HYTb.

FIG. 1 is a flow diagram showing the digestion of crustacean to form HYTb containing chitosan and glucosamine and HYTc which contains solid chitin. This figure also shows the subsequent processing of HYTc and HYTb with the microbial composition HQE to form HYTd, a solution with relatively high amounts of chitosan and glucosamine as compared to HYTb.

Briefly, in the arthropod biodegradation process a microbial composition is used to degrade the arthropod or waste components of the arthropod. It is a lactic acid fermentation process. The microbial composition contains microbes that produce enzymes that can degrade the chitin containing components of the arthropod to chitin, chitosan, N-acetyl glucosamine and glucosamine. It also contains microbes that produce enzymes that can degrade proteins and fats to produce amino acids and lipids. A preferred microbial composition for arthropod degradation is referred to as HQE. HQE was deposited with the American Type Culture Collection (ATCC) Manassas, Va., USA on Apr. 27, 2010 and given Patent Deposit Designation PTA-10861.

In a preferred embodiment, the marine arthropod is a crustacean and the preferred crustacean is shrimp. Shrimp by-product comprises shrimp cephalothorax and/or exoskeleton.

In the biodegradation process, it is preferred that the fermentation be facultative aerobic fermentation. It is also preferred that the fermentation is carried out at a temperature of about 30° C. to 40° C. The pH is preferably less than about 6, more preferably less than about 5.5. However, the pH should be maintained above about 4.3. The fermentation is carried out for about 24-96 hours. In some embodiments, the fermentation is carried out for about 24-48 hours and more preferably 24-36 hours. These fermentation times are far shorter than the typical prior art fermentation times of 10 to 15 days to achieve substantially the same amount of digestion, albeit without detectable formation of chitosan and glucosamine.

The separation of the mixture is preferably by centrifugation. (e.g. about 920 g). Gravity separation can also be used but is not preferred because of the time required to achieve separation.

The mixture separates in to three fractions: solid, aqueous and lipid. The aqueous fraction comprises protein hydroysate, amino acids, chitosan and The lipid fraction comprises sterols, vitamin A and E and carotenoid pigments such as astaxanthine.

As used herein, the term "HYTb" refers to the aqueous fraction and "HYTc" refers to the solid fraction obtained from the above biodegradation process. This process is described in U.S. Patent Application Ser. No. 61/289,706, filed Dec. 23, 2009 entitled "Biodegradation of Crustacean By-products", U.S. Patent Application Ser. No. 61/299,869, filed Jan. 1, 2010 entitled "Biodegradation Process and Microbial Composition" and U.S. Patent Application Ser. No. 61/355,365 filed Jun. 16, 2010 entitled "Biodegradation Process and Composition" each of which are incorporated by reference herein in their entirety. HYTb contains amino acids (about 12 wt %), chitosan (about 0.5-1.5 wt %), glucosamine (about 0.5-1.5 wt %) and trace elements (about 6 wt %) including calcium, magnesium, zinc, copper, iron and manganese. It also contains enzymes such as lactic enzymes, proteases, lipases, chitinases among others, lactic acid, polypeptides and other carbohydrates.

In addition to the uses described above for chitosan and glucosamine, HYTb alone or in combination with HYTc and the microbial composition HYTa are useful in the treatment of soil, seed, seedlings and foliage as disclosed in U.S. Patent Application Ser. No. 61/355,447 filed Jun. 16, 2010 entitled Microbial Process and Composition for Agricultural Use and U.S. patent application Ser. No. 13/160,333 filed Jun. 14, 2011 entitled Microbial Process and Composition, each of which are incorporated herein by reference in their entirety.

HYTd and the chitosan/glucosamine solutions obtained from the microbial digestion of chitin as described herein are similarly useful. See U.S. Patent Application 61/500,543 filed Jun. 23, 2011 entitled Agricultural Uses of HYTd.

It is preferred that HQE be used in the biodegradation process. In other embodiments, it is preferred that previously prepared HYTb be added to HQE or the fermentation broth. As described above, HYTb contains amino acids, chitosan, glucosamine and trace elements including calcium, magnesium, zinc, copper, iron and manganese. HYTb also contains enzymes such as lactic enzymes, proteases, lipases, chitinases, lactic acid, polypeptides and other carbohydrates. HYTb can also contain dormant microorganisms from a prior biodegradation process. Such microorganisms can become reactivated and, in combination with HQE, contribute to a more robust biodegradation process as compared to when HQE is used by itself as otherwise described herein More particularly, the process includes the following steps:

a. Activation of the microbial cells in a sugar base solution to enhance its growth and the biomass formation.

b. Milling of the shrimp by-products (cephalothorax and exosqueleton) to make a homogeneous paste.

c. Homogeneous mixing of the shrimp by-product paste with at least 10% of the activated inoculum.

d. Adjustment of the pH values to less than 6.0 in the mixture using a citric acid solution to inhibit the growth of micro organisms and to promote the development of microbial cells that constitute the inoculum.

e. Fermentation of the mixture in a non continuous agitated system at temperatures within a range of 30 to 40° C. at least for at least 96 hours maintaining pH at less than 5.0. The pH is monitored periodically. If the pH rises above 5.0, a citric acid buffer is added in an amount to maintain the pH below 5.0.

f. Centrifugation of the ferment to separate the three principal fractions: chitin, liquid hydrolysate and pigmented paste.

g. Rinsing of the crude chitin and recollection of the rinse water to recuperate fine solids or minerals.

h. Drying of the chitin and storage.

i. Drying and storage of the liquid hydrolysate.

j. The pigmented paste (lipid fraction) is stored in closed recipients for conservation.

The process and operational fundamentals are better understood with reference to the following detailed description.

Activation of Microbial Cells

The microbial compositions as disclosed herein are used as inoculum. The inoculum of HQE has a concentration of microbes of about 2.5 to 3.0% (w/v). HQE is activated by dilution to 5% in sugar cane solution (3.75% final concentration of sugar cane), and incubated at 37° C. for 5 days. HYTb (10 ml per liter of culture) is preferably added to provide a source of minerals and naturally derived amino acids. The cellular growth of the microorganisms was estimated by optical density measured at 540 nm. The activation is complete at an optical density of about 1.7. The concentration of microbes after activation is about 1.9 to 3.0% (w/v).

Preparation of Samples

The shrimp by-products samples are obtained from shrimp processing plants. Slightly thawed and minced residue (1500 g by batch) is mixed with 99 grams of sugar cane (final concentration 6.6% wt %) and 85.5 ml of activated HQE 5% (v/w) (optical density of cell=1.7). Then the pH is adjusted to 5.5 using 2 M citric acid.

Fermentation Control

The mixture is incubated at 36° C. with a non continuous agitation for 96 h. During the fermentation process, the pH is monitored by using a potentiometer, and the total titratable acidity (TTA, %) was determined by titration with 0.1 N NaOH until a pH of 8.5 is obtained. The TTA is expressed as a percentage of lactic acid.

Conditions of Separation

The fermentation product is a viscous silage which has an intense orange color, due to the astaxanthine presence. The ensilage is centrifuged (5° C.) at 1250 rpm (930 g) for 15 min to obtain the chitin, the liquid hydrolysates, and the pigment paste. The upper phase (pigment paste) is separated manually. The liquid hydrolysates are separated by decantation, and the sediment that constitutes the raw chitin is washed with distilled water to separate fine solids. The resulting liquid is collected and dried. The raw chitin, liquid hydrolysates and fine solids are dried at 60° C. All the fractions are stored to protect them from light.

2. Biodegradation of Chitin Containing Filamentous Fund, Yeast and Insects

Figure 3:
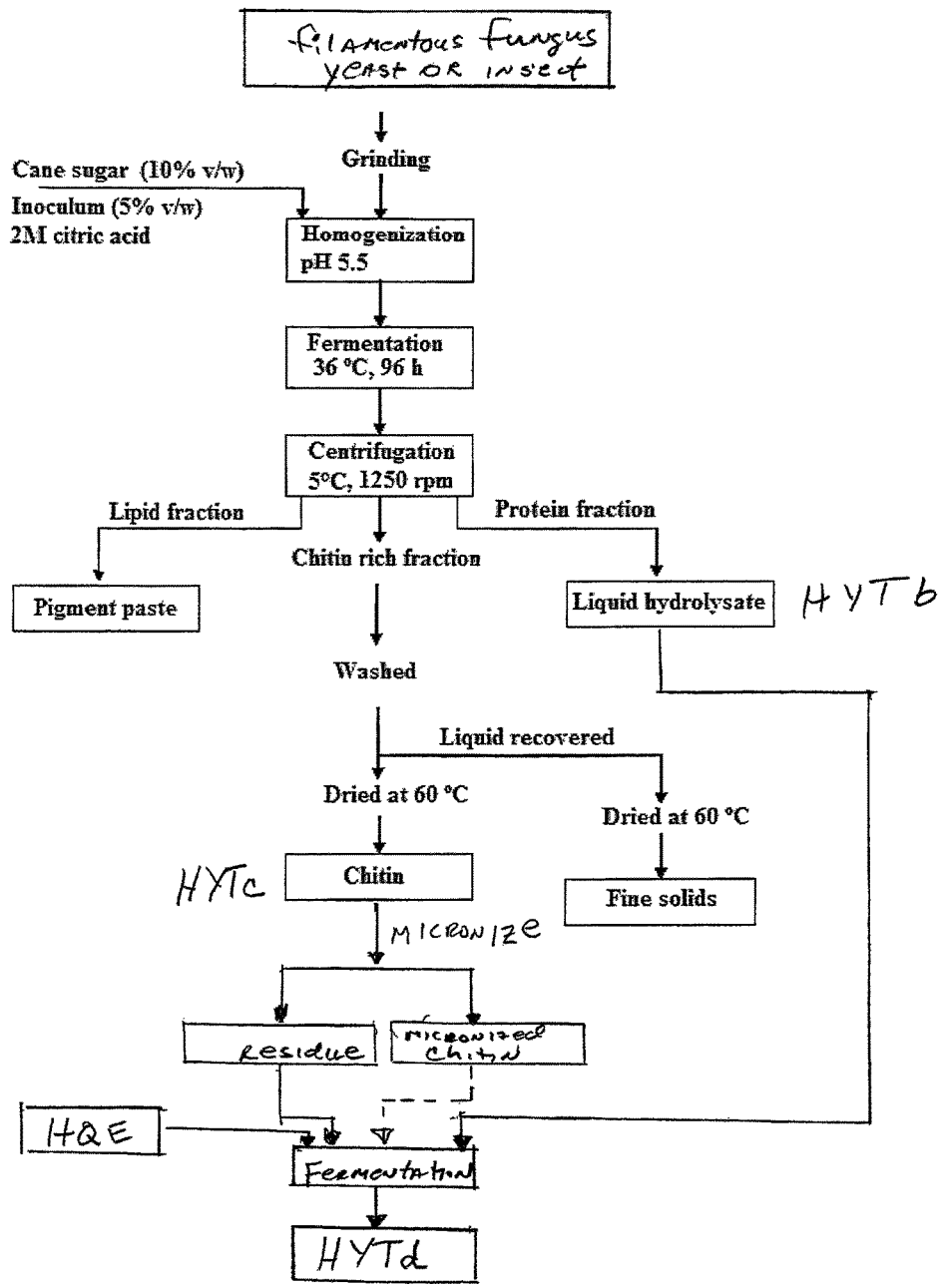
FIG. 3 is a flow diagram showing the digestion of fungi, including filamentous fungi, yeast and/or insects to form HYTb and HYTc. The HYTc and HYTb are optionally processed further with HQE to form HYTd, a solution with relatively high amounts of chitosan and glucosamine as compared to HYTb.

The same process is used to enzymatically degrade chitin containing filamentous fungi, yeast and/or insects. FIG. 3 is a flow diagram showing the digestion of filamentous fungi, yeast and/or insects to form HYTb and HYTc. The HYTc and HYTb are optionally processed further with HQE to form HYTd, a solution with relatively high amounts of chitosan and glucosamine as compared to HYTb.

Fungi, including filamentous fungi, and yeasts from groups including Zygomycetes, Basiomycetes, Ascomycetes and Deuteromycetes can be used in the biodegradation process. Examples include *Aspergillum, Penicillium, Trichoderma, Saccaromyces* and *Schizosacaromyces* species and edible mushrooms such as *Agaricus, Pleurotus, Boletus* and *Lentinula* species.

A preferred microbial composition to digest fungi, including filamentous fungi, yeasts and insects is HQE 3. Chemical Extraction from Fund and/or Yeasts The source of chitin need not be from HYTc. For example, chitin derived from fungi, including filamentous fungi, and/or yeasts can be used. For example, U.S. Pat. No. 7,556,946 discloses a chemical process to extract chitin from fungi, including filamentous fungi, and yeasts from groups including Zygomycetes, Basiomycetes, Ascomycetes and Deuteromycetes. Examples include *Aspergillum, Penicillium, Trichoderma, Saccaromyces* and *Schizosacaromyces* species and edible mushrooms such as *Agaricus, Pleurotus, Boletus* and *Lentinula* species.

Chitin Digesting Microbial Compositions

1. HQE Consortium

HQE was deposited with the ATCC on Apr. 27, 2010 and Given Patent Deposit Designation PTA-10861.

HQE was developed, in part, for the biodegradation of chitin containing marine Arthropods such as crustaceans. However, it has been determined that HQE can also be used to enzymatically convert solid chitin into chitosan and glucosamine. It is believed that other microbial compositions as disclosed herein can be used in the processes disclosed herein.

The following are the microorganisms in HQE which are believed to be involved in the biodegradation process and their known properties. In some cases the strain is identified as "Bioderpac, 2008". Where the species is not known, the species and strain are identified as "Bioderpac, 2008"

*Bacillus subtilis* (SILoSil® BS) is a Gram positive bacterium which is mesophilic and grows at an optimum temperature between 25 and 35° C. It is aerobic and can grow in anaerobic conditions and utilizes a wide variety of carbon sources. It contains two nitrate reductases, one of which is utilized for nitrogen assimilation. It is capable of secreting amylase, proteases, pullulanases, chitinases, xilanases and lipases.

*Bacillus thuringiensis* (Strains HD-1 and HD-73 (SILoSil®BT)) are Gram Positive anaerobic facultative bacteria, in the form of peritrichous flagella. Strains HD-1 and HD-73 synthetizes crystals with diverse geometric forms of proteic and insecticide activity during the spore period. Strains HD-1 and HD-73 secret exochitanases when in a chitin containing medium and can be utilized for the degradation of the crustacean residues during the production of chitooligosaccharides.

*Bacillus cereus* (Bioderpac, 2008) is an aerobic facultative bacterium, gram positive, and spore forming. It is mesophilic and grows at an optimum temperature between 20 and 40° C. It produces the antibiotics zwittermicin A and kanosamin.

*Bacillus licheniformis* (Bioderpac, 2008) is a Gram-positive, motile, spore forming and facultative anaerobic bacterium. It produces bacitracin, alpha amylases, lactamases, proteases and alkaline phosphatases. This is a non-pathogen microorganism that is associated with plants or plant materials.

*Bacillus megaterium* (Bioderpac, 2008) is a Gram-positive aerobic bacterium. It is considered a saprophyte. It produces glucose dehydrogenase, penicillin amydase, beta-amidase and neutral proteases.

*Lactobacillus acidophilus* (Bioderpac, 2008) is a member of one of the eight species of lactic acid bacteria. It is Gram positive, non-sporulating and produces lactic acid during fermentation that utilizes lactose as a principal source of carbon to produce energy. It grows with or without the presence of oxygen in an acidic medium (pH 4-5). It produces the bactereocins named lactacin B, organic acids, diacetyls and hydrogen peroxide.

*Lactobacillus casei* (Bioderpac, 2008) is a mesophilic, facultative anaerobic which is Gram positive and non-spore forming. It has the ability to adapt to cold temperatures. The optimum pH for its growth is 5.5. It ferments galactose, glucose, fructose, mannose, mannitol, and acetylglucosamine. This species can be grown over a wide range of pH and temperature. It produces amylase enzymes. It inhibits the growth of pathogenic bacteria such as H. pylori by reducing pH through the production of (1) organic acids such as acetic, proprionic or lactic acid or (2) hydrogen peroxide. This microorganism secretes bacterocines.

*Pseudomonas fluorescens* (Bioderpac, 2008) is a bacterium with multiple flagellum, forced aerobic and its optimal temperature for growth is between 25 and 35° C. It produces thermostable lipases and proteases. It is antagonist towards a large number of soil fungus strains. It produces secondary metabolites such as antibiotics, iron chelates, and cyanides.

It produces endochitanase and cellulase in mediums with different glucose concentrations.

*Trichoderma harzianum* (TRICHOSIL) is a saprophyte fungus. It exhibits antibiotic action and biological competition and for this reason has biological control properties. It produces enzymes that degrade cell walls or a combination of such activities. It produces glucanases, chitinases, lipases, and extracellular proteases when it interacts with some pathogenic fungi, such as Fusarium.

*Rhizobium japonicum* (Bioderpac, 2008) is a nitrogen fixating bacteria. It synthesizes a hydrogenase system that participates in the recycling of hydrogen to avoid its loss during nitrogen fixation.

*Azotobacter vinelandii* (Bioderpac, 2008) is an aerobic bacterium. It produces nitrogenases and is capable of nitrogen fixation.

*Clostridium pasteurianum* (Bioderpac, 2008) is a Gram positive bacteria, anaerobic obligated. It produces ferroxine (an electron transporting protein) that acts as a direct electron donor in the reduction of proteic iron.

*Proteus vulgaris* (Bioderpac, 2008) Is a gram positive bacteria, anaerobic, facultative that grows at temperatures close to 23° C. It proteolytically degrades proteins to free amino acids by the enzymes it produces.

*Streptomyces* sp. (Bioderpac, 2008) is a Gram-positive soil bacterium. It produces multiple enzymes that metabolize diverse nutrients. It can survive significant changes in temperature, humidity and nutrient sources. The extracellular enzymes produced by these bacteria utilize chitin and chitosan as substrates at a pH of 4.5 to 6.5 and at 60° C. These are conditions generated at the beginning and at the end stages of lactic fermentation in the biodegradation process.

*Nitrobacter* sp. (Bioderpac, 2008) is Gram negative bacteria, aerobic, which converts nitrites into nitrates. It grows at a pH between 6 and 9 and at temperatures between 10 to 34° C. The bacteria degrade organic polymers such as chitin into compounds that are utilized by other organisms, such as *Pseudomonas* fluorescens and *Rhizobium japonicum* (Bioderpac2008).

*Micrococcus* sp. (Bioderpac, 2008) is a spheric Gram positive bacterium. This microorganism in association with *Streptomyces* sp ( ) is capable of degrading colloidal chitin derivatives.

HQE can be used to enzymatically digest chitin. However, of these microbes, it is believed that one, two, three, four or more of the following can be isolated from HQE and used to degrade chitin into chitosan and glucosamine: *Bacillus subtilis* ((SILoSil®BS), *Bacillus thuringiensis* (Strains HD-1 and HD-73 (SILoSil®BT), *Pseudomonas fluorescens* (Bioderpac, 2008), *Trichoderma harzianum* (TRICHOSIL), *Streptomyces* sp. (Bioderpac, 2008), and *Micrococcus* sp. (Bioderpac, 2008). In preferred embodiments the microbial composition contains at least one of, at least two of and preferably each of *Bacillus subtilis* (SILoSil®BS), *Bacillus thuringiensis* (Strains HD-1 and HD-73 (SILoSil®BT) and *Trichoderma harzianum* (TRICHOSIL). In yet another preferred embodiment, the microbial composition comprises *Trichoderma harzianum* (TRICOSIL).

2. Groups and Enzymatic Activity of Microorganisms in HQE

The biodegradation of the components of chitin containing arthropods, fungi, filamentous fungi, yeast and/or insects requires hydrolytic enzymes such as proteases, lipases, and chitinases. The following groups and combinations of groups are also useful for the digestion of chitin into chitosan and glucosamine.

The primary group of microbes in HQE comprises *Lactobacillus acidophilus* (Biodepac 2008), *Bacillus subtilis* (SILoSil®BS), *Pseudomonas fluorescens* (Biodepac 2008), *Bacillus licheniformis* (Biodepac 2008) and *Trichoderma harzianum* (TRICHOSIL). These microorganisms are capable of biodegrading arthropod or arthropod by-products. One or more of the members of this primary group also have a synergistic action when combined with other microorganisms from HQE.

The first group of microorganisms includes microorganisms which cause the reduction of pH and which stabilize fermentation due to the production of organic acids and hydrogen peroxide. This group includes *Lactobacillus acidophilus* (Biodepac 2008) and *Lactobacillus casei* (Bioderpac 2008). Their activity is important at the start of fermentation and during the final stages of fermentation to produce the optimum pH for the hydrolytic enzymes. Their activity also creates a culture environment which prevents the growth of unwanted microorganisms and favors the demineralization of the chitin residues. *Lactobacillus acidophilus* (Biodepac 2008) is a member of the primary group.

The second group of microorganisms includes microorganisms which produce extracellular enzymes. This second group includes *Bacillus subtilis* (SILoSil®BS), *Bacillus cereus* (Biodepac 2008), *Trichoderma harzianum* (TRICHOSIL), *Rhizobium japonicum* (Biodepac 2008) and *Azotobacter vinelandii* (Biodepac 2008). The chitin chains in arthropod or arthropod by-products are associated with protein molecules. The separation of such polymers requires the hydrolytic action obtained from the chitinolytic and proteolytic enzymes produced by these microorganisms. Both types of enzymes break the chains on the internal portion of the polymer to produce oligomers of diverse sizes. The action from these enzymes occurs in a successive manner within the intermediate and final phases of the fermentation process when the appropriate pH conditions are achieved. The microorganisms on this group and the environmental conditions they produce facilitate the liberation of pigments and the lipid fraction adhered to these residues. *Bacillus subtilis* (SILoSil®BS) and *Trichoderma harzianum* (TRICHOSIL) are members of the primary group.

The third group of microorganisms includes the microorganisms *Bacillus licheniformis* (Biodepac 2008), *Pseudomonas fluorescens* (Biodepac 2008), *Streptomyces*, (Biodepac 2008) and *Clostridium* (Biodepac 2008). These microorganisms hydrolyze oligomers (chito-oligosaccharides and peptides) to produce chitobioses, glucosamine, and free amino acids. *Bacillus licheniformis* (Biodepac 2008) and *Pseudomonas fluorescens* (Biodepac 2008) are members of the primary group.

In preferred embodiments, one or two of the first, second and third groups of microorganisms can be combined. Alternatively, all of the first, second and third groups can be combined.

A fourth group of microorganisms includes *Bacillus thuringiensis* (strains HD-1 and/or HD-73), *Streptomyces* (Bioderpac, 2008), *Micrococcus* (Bioderpac, 2008), *Nitrobacter* (Bioderpac, 2008) and *Proteus vulgaris* (Bioderpac, 2008). The fourth group of microorganisms can be combined with (1) the primary group of microorganisms (2) any of the first, second and third groups of microorganisms (3) the combination of one or two of the first, second and third groups of microorganisms or (4) the combination of all of the first second and third groups. The addition of this fourth group results in a synergistic effect which enhances the biodegradation process.

Each of these groups, including the primary group, is separately useful and can be combined with prior art microbial compositions to enhance their performance. In this regard, the fourth group is particularly preferred.

Table 1 sets forth some of the aforementioned combinations. Column 1 is a list of the known microorganisms in HQE that are believed to be active in the biodegradation process. Column 2 lists the microorganisms from column 1 without the microorganisms in the fourth group of microorganisms. Column 3 shows the combination of the primary microorganisms while columns 4, 5 and 6 identify the combination of microorganisms from the first, second and third groups. Column 4 is the combination of groups 1 and 2; column 5 of groups 1 and 3 and column 6 groups 2 and 3. Other useful combinations are set forth in columns 7-10.

TABLE 1

| Microorganism | 1 | 2 | 3 | 4 | 5 | 6 | 7 | 8 | 9 | 10 |
|---|---|---|---|---|---|---|---|---|---|---|
| Bacillus subtilis | X | X | X | X |   | X | X | X |   | X |
| Bacillus cereus | X | X |   | X |   | X |   | X |   | X |
| Bacillus megaterium | X | X |   |   |   |   |   |   |   |   |
| Azotobacter vinelandii | X | X |   | X |   | X |   | X |   | X |
| Lactobacillus acidophilus | X | X | X | X | X |   | X | X | X |   |
| Lactobacillus casei | X | X |   | X | X |   |   | X | X |   |
| Trichoderma harzianum | X | X | X | X |   | X | X | X |   | X |
| Rhizobium japonicum | X | X |   | X |   | X |   | X |   | X |
| Clostridium pasteurianum | X | X |   |   | X | X |   |   | X | X |
| Bacillus licheniformis | X | X | X |   | X | X | X |   | X | X |
| Pseudomonas fluorescens | X | X | X |   | X | X |   |   |   |   |
| Bacillus thuringiensis | X |   |   |   |   | X | X | X | X | X |
| Streptomyces | X |   |   |   |   | X | X | X | X | X |
| Nitrobacter | X |   |   |   |   |   | X | X | X | X |
| Micrococcus | X |   |   |   |   |   | X | X | X | X |
| Proteus vulgaris | X |   |   |   |   |   | X | X | X | X |

Particularly preferred cultures are 1-4, 6-8 and 10

The activity of the enzymatic extracts produced by the microorganisms within HQE is complex, but has permitted the degradation of the chitinous residues of arthropods such as crustaceans. The microorganisms in HQE are activated in a successive manner according to the environment generated by the organisms used.

HYTb

HYTb contains amino acids (about 12 wt %), chitosan (about 0.5-1.5 wt %), glucosamine (about 0.5-1.5 wt %) and trace elements (about 6 wt %) including calcium, magnesium, zinc, copper, iron and manganese. It also contains enzymes such as lactic enzymes, proteases, lipases, chitinases among others, lactic acid, polypeptides and other carbohydrates. In some embodiments, the degree of acetylation of the produced chitosan is 20% or less, preferably 15% or less, more preferably 10% or less, still more preferably preferable 8% or less and most preferably 5% or less. The specific gravity of HYTb is typically about 1.050-1.054. The average amino acid content in HYTb for certain amino acids is set forth in Table 2.

TABLE 3

Amino acid profile dry powder hydrolysates (mg per g dry weight)

| Amino acid | Dry powder hydrolysates |
|---|---|
| Aspartic acid | 38 |
| Glutamic acid | 39 |
| Serine | 16 |
| Histidine | 9 |
| Glycine | 28 |
| Threonine | 14 |
| Alanine | 36.1 |
| Proline | 25.8 |
| Tyrosine | 70 |
| Arginine | 22.2 |
| Valine | 20 |
| Methionine | 16.4 |
| Isoleucine | 18.3 |
| Tryptophan | 3.1 |
| Leucine | 23 |
| Phenylalanine | 39 |
| Lysine | 13 |
| Total | 431 |

The primary component of HYTc is chitin. It has an average molecular weight of about 2300 Daltons and constitutes about 64 wt % of the composition. About 6% of HYTc contains minerals including calcium, magnesium, zinc, copper, iron and manganese, about 24 wt % protein and 6% water. It has a specific gravity of about 272 $Kg/m^3$.

HYTd

HYTd is obtained by fermenting chitin with a microbial composition suspended in HYTb. HYTb already contains chitosan (about 0.5-1.5 wt %) and glucosamine (about 0.5-1.5 wt %). The amount of chitosan and glucosamine in HYTd ranges from about 2 wt % to 2.5 wt % chitosan and from about 2 wt % to 5 wt % glucosamine. This represents an increase in the amount of chitosan and glucosamine as compared to HYTb of about 0.5 wt % to 2.5 wt % chitosan and from about 0.5 wt % to 5 wt % glucosamine.

As used herein the term "glucosamine" includes glucosamine or a mixture of glucosamine and N-acetyl glucosamine. In most embodiments, HYTd contains glucosamine and N-acetyl glucosamine.

HYTd can also contain particulate chitin that has not been completely digested. In general the fermentation mixture is filtered to remove large particles of chitin. The filtrate contains usually no more that 2 wt % chitin.

HYTd when undiluted is similar to HYTb in that it contains amino acids (about 12 wt %) and trace elements (about 6 wt %) including calcium, magnesium, zinc, copper, iron and manganese. It also contains enzymes such as lactic enzymes, proteases, lipases, chitinases among others, lactic acid, polypeptides and other carbohydrates. In some embodiments, the degree of acetylation of the produced chitosan is 20% or less, preferably 15% or less, more preferably 10% or less, still more preferably preferable 8% or less and most preferably 5% or less. The average amino acid content in HYTd for certain amino acids is similar to HYTb. See Table 2.

HYTd preferable comprises 12 wt % L-amino acids (Aspartic acid, Glutamic acid Serine, Histidine, Glycine, Threonine, Alanine, Proline, Arginine, Valine, Methionine, Isoleucine, Tryptophan, Phenylalanine, Lysine and threonine) and 5 wt % glucosamine and chitosan. HYTd also preferable contains one or more or all of soluble minerals (P, Ca, Mg, Zn, Fe and Cu), enzymes and lactic acid from the chitin digestion process as well as other polysaccharides.

The fermentation mixture, e.g. HYTb and HQE, can be diluted at the beginning of the chitin digestion process. If diluted, the ration of chitosan and/or glucosamine to amino acids will be higher in the HYTd produced after digestion. That is dilution before fermentation produces relatively more chitin and/or glucosamine taking into account the dilution factor than if no dilution occurs.

Chitosan/Glucosamine Products

When the starting fermentation mixture does not contain chitosan and glucosamine, e.g. when activated HQE is used to digest chitin, the amount of chitosan and glucosamine in the final product ranges from about 0.5 wt % to 1.0 wt % chitosan and from about 0.5 wt % to 1.8 wt % glucosamine.

Example 1

Production of Chitosan Oligosaccharides and Glucosamine

Chitosan oligosaccharides and glucosamine can be produced under different condition. The hydrolysis time can be varied to find the optimal conditions to produce chitosan and/or glucosamine.

Manual agitation three times a day was used in each of the following experiments. The temperature was 35° C.

TABLE 2

| Treatment | Chitin (HYT-C) | Amino acid (HYT-B) | Inoculums Activated for 3 days (HQE) |
|---|---|---|---|
| 1 | 2% -- 20 g | 1000 ml | 0 ml |
| 2 | 3% -- 30 g | 1000 ml | 0 ml |
| 3 | 4% -- 40 g | 1000 ml | 0 ml |
| 4 | 2% -- 20 g | 970 ml | 30 ml |
| 5 | 3% -- 30 g | 970 ml | 30 ml |
| 6 | 4% -- 40 g | 970 ml | 30 ml |
| 7 | 3%, micronized chitin | 1000 ml | 0 ml |

Quantification of Glucosamine

The analysis of glucosamine is determinate as previously reported Tsuji et al. (1969), with some modifications: Specifically, to a sample of 300 µl, 300 µl KHSO4 (5%), 300 µl NaOH2 (5%), is add. The mixture is then left standing with occasional shaking for 15 min. The excess of nitrous acid is removed by adding 300 µl NH$_4$SO$_3$ NH$_2$ (12.5%). 300 µl MBTH (0.5%) is added to the mixture and incubate in a water bath for 60 min. Finally, 00 µl FeCl$_3$ (0.5%) is add and the absorbance at 653 was read after 30 min against a blank containing water.

Example 2

The following protocol can be used for industrial level production of HYTd with the high concentrations of glucosamine and chitosan. The following table shows the parameters used. The amount of activated HQE is proportional to that used in Example 1.

TABLE 3

| Parameters of Industrial production | |
|---|---|
| Carrier solution: HYT-B | 15,000 L |
| Micronized chitin (residuary chitin of milling process) | 300 kg |
| Temperature | Room temperature (30-35° C.) |

TABLE 3-continued

| Parameters of Industrial production | |
|---|---|
| Agitation | 8 hours/daily |
| Production time | 7 days |

Example 3

Production Kinetics

Table 4 shows the production of glucosamine in HYTd as a function of time. Chitin (20 grams) was digested with 30 ml of activated HQE in 970 ml of HYTb.

TABLE 4

| Production days | % total of glucosamine (HYTd) | Glucosamine in HYTb | Glucosamine produced |
|---|---|---|---|
| 3 | 1.11 | 0.74 | 0.37 |
| 4 | 1.54 | 0.74 | 0.8 |
| 6 | 1.78 | 0.74 | 1.04 |
| 7 | 1.93 | 0.74 | 1.19 |
| Days of packaging (approx 20 days) | 2.29 | 0.74 | 1.55 |

Figure 2:
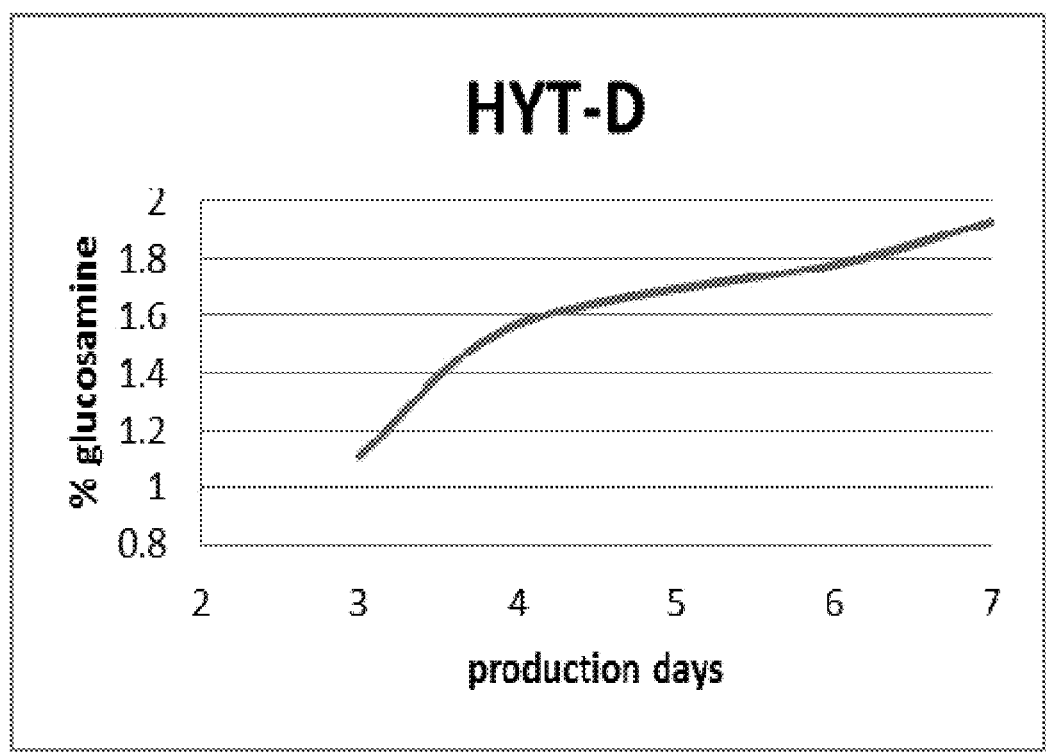
FIG. 2 depicts the formation of glucosamine as a function of time as compared to HYTb.

The results from this experiment are also depicted in FIG. 2.

Example 3

Figure 4:
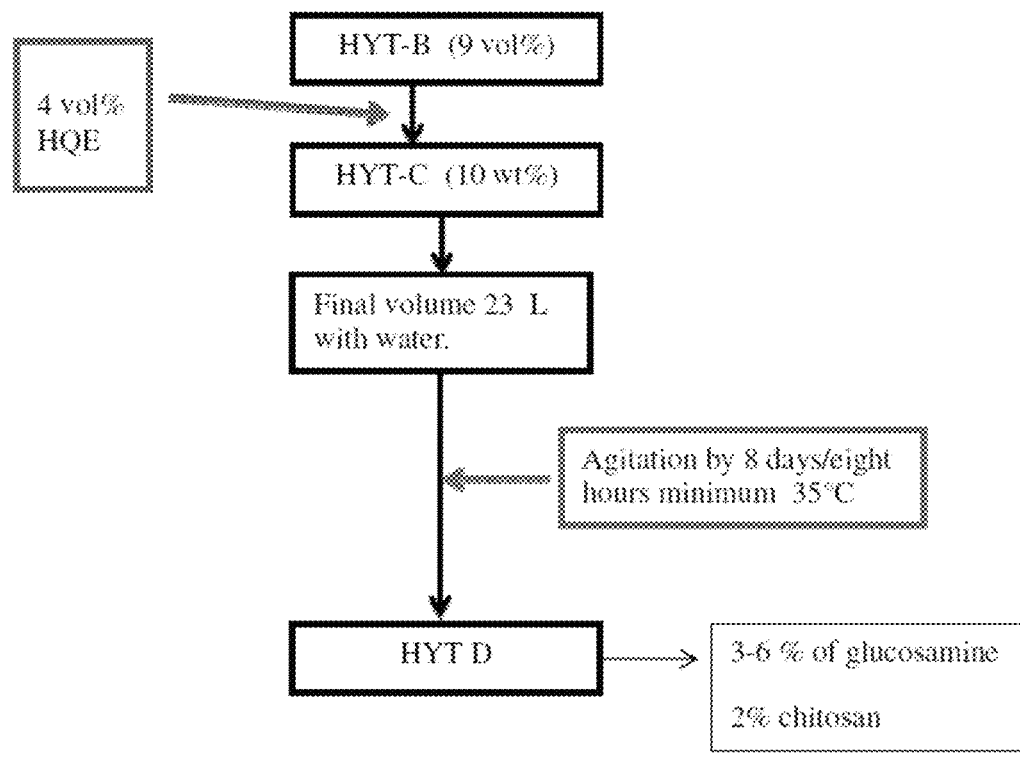
FIG. 4 depicts a process for making HYTd.

One kilogram of residual chitin from HYTc was combined with two liters of HYTb. One liter of activated HQE was added. After mixing, twenty liters of water was added. The resulting mixture was fermented for six days at 35 to 36 degrees Celsius. This resulted in a solution containing 6 wt % glucosamine and 2 wt % chitosan. See FIG. 4.

What is claimed is:

1. A process for increasing the chitosan and/or glucosamine in HYTb comprising:
    forming a mixture comprising HYTb, a microbial composition and solid chitin, wherein said microbial composition comprises HQE (PTA-10861), and said microbial composition comprises one or more microbes that produce chitin digesting enzymes;
    and fermenting said mixture for a time sufficient to enzymatically digest all or part of said chitin to form a fermented mixture wherein the amount of at least one of chitosan and glucosamine in said fermented mixture is greater than in said HYTb.

2. The process of claim 1 wherein said mixture is diluted to form a diluted mixture and said diluted mixture is fermented to digest all or part of said chitin to form a fermented mixture, wherein the absolute amount of at least one of chitin and glucosamine in said fermented mixture is greater than that in said HYTb.

3. The process of claim 1 wherein HYTc is the source of said chitin.

4. The process of claim 3 wherein said HYTc is micronized to form micronized chitin and residual chitin and said chitin comprises said residual chitin.

5. The process of claim 1 further comprising separating solids and optionally the microbes and cells from said fermented mixture.

6. A process comprising:
mixing a marine animal or marine animal by-product with a first microbial composition to form a first mixture, wherein said first microbial composition contains one or more microbes that produce enzymes that digest said marine animal or by-product into solid, aqueous and lipid fractions, wherein said solid fraction comprises chitin and said aqueous phase comprises amino acids, chitosan and glucosamine;
fermenting said first mixture to form a first fermented mixture;
separating said first fermented mixture into a first solid fraction, a first aqueous fraction and a first lipid fraction;
forming a second mixture comprising said first aqueous fraction, chitin and a second microbial composition wherein said second microbial composition comprises HQE (PTA-10861), and wherein said microbial composition comprises one or more microbes that produce chitin digesting enzymes;
fermenting said second mixture to form a fermented second mixture; and
optionally, separating said fermented second mixture into a second aqueous and second solid fraction, wherein said second aqueous fraction has a higher content of at least one of chitosan and glucosamine as compared to said first aqueous fraction.

7. The process of claim 6 wherein said second mixture is diluted to form a diluted second mixture and said diluted second mixture is fermented to digest all or part of said chitin to form a second fermented mixture, wherein the absolute amount of at least one of chitin and glucosamine in said second fermented mixture is greater than that in said first aqueous fraction.

8. The process of claim 6 wherein HYTc is the source of said chitin.

9. The process of claim 8 wherein the HYTc is micronized to form micronized chitin from HYTc and residual chitin from HYTc and the residual chitin from HYTc is the source of said chitin.

10. The process of claim 6 further comprising separating solids and optionally the microbes and cells from said fermented second mixture.

11. The process of claim 6 wherein said first microbial composition comprises HQE.

* * * * *